United States Patent
Moncada et al.

(10) Patent No.: US 10,144,817 B2
(45) Date of Patent: *Dec. 4, 2018

(54) ACTIVE AND INTELLIGENT ADDITIVE, POLYMER AND ARTICLE

(71) Applicants: Braskem S.A., Camacari (BR); Universidade Federal do Rio Grande do Sul, Porto Alegre (BR)

(72) Inventors: Edwin Moncada, Porto Alegre (BR); Joao Henrique Zimnoch dos Santos, Porto Alegre (BR); Larissa Brentano Capeletti, Campo Bom (BR)

(73) Assignees: Brasksm S.A., Camacari, BA (BR); Universidade Federal do Rio Grande do Sul, Porto Alegre, RS (BR)

( * ) Notice: Subject to any disclaimer, the term of this patent is extended or adjusted under 35 U.S.C. 154(b) by 0 days.

This patent is subject to a terminal disclaimer.

(21) Appl. No.: 15/625,615

(22) Filed: Jun. 16, 2017

(65) Prior Publication Data

US 2017/0283592 A1    Oct. 5, 2017

Related U.S. Application Data

(63) Continuation-in-part of application No. 13/822,553, filed as application No. PCT/BR2011/000323 on Sep. 13, 2011, now Pat. No. 9,700,054.

(30) Foreign Application Priority Data

Sep. 13, 2010  (BR) ...................................... 1005460

(51) Int. Cl.

| C08K 9/10 | (2006.01) |
| A01N 25/10 | (2006.01) |
| G01N 21/78 | (2006.01) |
| C08J 5/18 | (2006.01) |
| C08K 9/06 | (2006.01) |
| C08K 3/10 | (2018.01) |
| C08K 3/30 | (2006.01) |
| C08K 5/092 | (2006.01) |
| C12Q 1/04 | (2006.01) |
| G01N 31/22 | (2006.01) |
| C08K 3/16 | (2006.01) |
| C08K 5/00 | (2006.01) |
| A01N 43/08 | (2006.01) |
| A01N 59/02 | (2006.01) |
| A01N 59/20 | (2006.01) |
| C08L 23/02 | (2006.01) |

(52) U.S. Cl.
CPC ................ C08K 9/10 (2013.01); A01N 25/10 (2013.01); C08J 5/18 (2013.01); C08K 9/06 (2013.01); G01N 21/783 (2013.01); *C08J 2323/04* (2013.01); *C08J 2323/10* (2013.01); *C08K 3/10* (2013.01); *C08K 3/16* (2013.01); *C08K 3/30* (2013.01); *C08K 5/0058* (2013.01); *C08K 5/092* (2013.01); *C12Q 1/04* (2013.01); *G01N 31/223* (2013.01)

(58) Field of Classification Search
CPC .......... C08L 23/12; C08L 23/02; C08K 3/10; C08K 5/092; C08K 5/54; C08K 9/10; C08K 3/30; C08K 3/015; C08K 5/0058; A01N 37/36; A01N 59/02; A01N 59/20; A01N 25/00; A01N 25/10; C12Q 1/04; G01N 21/783; G01N 31/223

See application file for complete search history.

(56) References Cited

U.S. PATENT DOCUMENTS 9,700,054 B2 *  7/2017  Moncada ............... A01N 25/00

* cited by examiner

*Primary Examiner* — Mark V Stevens
(74) *Attorney, Agent, or Firm* — DuaneMorris LLP

(57) ABSTRACT

The present invention relates to active and intelligent additives having hybrid characteristics, that are compatible with polymers, are thermally and mechanically stable, are capable of releasing electrons and/or photons in the presence of chemical compounds, specifically amino compounds, amide compounds, oxygen reducing compounds, water or vapors thereof. The active and intelligent additives incorporate themselves into polymer matrices allowing the obtainment of active and intelligent polymeric articles. These active and intelligent polymeric articles may act as inhibitors of growth of microorganisms and fungi, as well as indicators of the presence of gasses, either in the atmosphere or caused by the decomposition of foodstuffs, for example.

7 Claims, 2 Drawing Sheets

ACTIVE AND INTELLIGENT ADDITIVE, POLYMER AND ARTICLE

CROSS REFERENCE TO RELATED APPLICATION

This application is a continuation-in-part of U.S. application Ser. No. 13/822,553, which was filed in the United States Patent and Trademark Office on Mar. 12, 2013.

TECHNICAL FIELD

The present invention relates to active and intelligent additives having hybrid characteristics, that are compatible with polymers, are thermally and mechanically stable, are capable of releasing electrons and/or photons in the presence of chemical compounds, specifically amino compounds, amide compounds, oxygen reducing compounds, water or vapors thereof. The active and intelligent additives incorporate themselves into polymer matrices allowing the obtainment of active and intelligent polymeric articles. These active and intelligent polymeric articles may act as inhibitors of growth of microorganisms and fungi, as well as indicators of the presence of gasses, either in the atmosphere or caused by the decomposition of foodstuffs, for example.

PRIOR ART

The constant and increasing concern with the safety of the population towards attempting to warrant healthy work environments, foodstuffs evidencing good physical, chemical and nutritional characteristics, the avoidance of pro-positive contamination (bio-terrorism), among others, has been producing innumerous researches for the obtainment of specific sensors that might allow the identification and/or the control of some of such scenarios. It is therefore most important to monitor working environments, for example, in some mining companies, chemical and pharmaceutical companies, viral research laboratories, foodstuffs production and consumption environments, among others, to warrant better life conditions for the workers in addition to warranting high quality products for the consumers and for the public in general. Problems such as pro-positive contamination of foodstuffs by dangerous substances (ANTHRAX, viruses, toxic metals, among others) may be identified by means of the use of sensors that allow, in some cases, to attack (viruses), or in other cases to detect and communicate (Anthrax and metals), providing totally secure conditions and a better life quality to the population.

Thus, also active and intelligent compounds, in addition to having the necessary characteristics to monitor the previously mentioned conditions, may be used to extend the useful live of perishable foodstuffs (acting against microorganisms) and/or to communicate the quality state of the foodstuff, whereby such compounds would allow the supply of totally healthy foodstuffs and confirm the quality characteristics thereof. In the foods packing industry there have been used some additives that are incorporated into the packaging materials (paper, plastic, etc.) that evidence some of the characteristics previously mentioned herein or that might potentially act as cited above upon being dispersed within packaging materials.

In patent application No. US 2009/0011160 A1 there are disclosed polymeric films on which chitosan has been immobilized on at least one of their surfaces. Such layer of chitosan is said to be substantially resistant to leaching and to have a strong antimicrobial activity. The application of the chitosan is made on a biaxially orientated polypropylene film by plasma activation of the surface at atmospheric pressure. Those films are then used in antimicrobial active food packaging systems. Chitosan is a compound that is sensitive both to temperature and to mechanical processing, whereby the application thereof onto the polymeric film is required to be performed only after the fabrication of the film, and further to be combined with the incidence of plasma, which implies more than one step, a higher cost and greater complexity in processing.

In turn, patent application No. US 2006/0083710 A1 also discloses the use of a chitosan coating for polymeric articles, however there are grafted amino-reactive functional groups on the surface of the polymer prior to deposition of the chitosan layer. For such final coating, there occurs a reaction of the amino groups of the chitosan with the amino-reactive groups grafted on the surface of the polymer, stabilizing the chitosan layer and causing the same to be at a necessary concentration to reduce microbial growth. In the same manner as in the previously cited patent application, there is a need of more than one step in the process (grafting and application of chitosan onto the film), which entails implications in terms of cost and complexity of the process.

In patent application No. US 2007/0166399 A1 there are also claimed polymeric articles having antimicrobial activity, particularly packages, however using as active ingredient silver compounds containing silver sulfate, as well as the methods of manufacture thereof, including methods to whiten the articles and packages obtained by means of stabilization of the silver sulfate. There is further described that the silver compound layer, including silver sulfate, is sealed within the article or package having antimicrobial properties. It is known that silver is under study regarding its toxicity, which fact impacts the use thereof on packages intended for foodstuffs.

In international publication No. WO 96/23022 A1 there is disclosed the use of a combination of terpenes or terpene derivatives with vitamins that are different from those terpenes as coatings having an antioxidant function. Such action occurs by means of electron transfer reactions between the cited compounds and the oxidizer that is present. Among the vitamins that are used there are included Vitamin A and carotenes, and the substrates that are possible to use for such coating are inorganic materials, natural materials, thermoplastic materials and thermosetting materials. Once again, these compounds are applied to the articles upon the same being ready, which fact implies further steps and complexity of the process.

In patent application No. US 2005/0164169 A1 there is described the use of surface plasmon resonance for generating antibacterial, antimicrobial, hydrophilic, hydrophobic, anti-adhesive, adhesive, biological and catalytic properties, among others. There is claimed a method of nonlinear generation using light with wavelengths ranging from X-ray to infrared, in order to enhance the plasma (surface electrons) generation by nanometer-sized particles of noble metals or semiconductors such as silver, copper, platinum, etc. Among the possible applications there may be pointed out the use as a bactericide, in corrosive preventing paints, in medical applications and building materials. Although the treatment applied on the surface of the film consists in only one step, it still represents an extra step after the preparation of the said film.

Thus, the present invention introduces a novel active and intelligent additive, which in addition to exhibiting the desired characteristics of activity on the final product, such as the inhibition of growth of microorganisms and fungi, and the indication of the presence of analytes (gasses) and absence of toxicity, further adds the advantage of being easily incorporated to the polymeric matrix due to its hybrid property which provides compatibility with the polymer. Such fact renders possible the obtainment of articles, such as films, from the additized polymer.

Therefore, the present invention is related to an active and intelligent additive that is compatible with polymers and which has a mode (or mechanism) of antimicrobial and indicative action that is different from the mechanisms found in the prior art.

Grounds of the Invention

The present invention refers to active and intelligent additives, formed by a sensitive compound encapsulated in an inorganic matrix with hybrid characteristics, that are thermally and mechanically stable, and are capable of releasing electrons and/or photons in the presence of chemical compounds. The present invention also consists in the application of these additives to polymeric matrices whereby the resulting material may be useful in situations in which it is necessary to know the conditions of the environment and prevent the proliferation of bacteria. Moreover, the additives according to the present invention may be applied to non-polar polymers used in the field of communications by way of electronic means and in the generation of energy and change of the electrical properties of the material by means of the release of electrons. Those characteristics can find applicability in industries such as in pharmaceuticals, communications, power generation, electronics, and petrochemicals, medical and environmental industries, among others.

In the present invention the active and intelligent additives may be defined as constituting devices that are capable of releasing electrons and/or photons when they interact with certain chemical compounds. The electrons and/or photons release process occurs by way of a chemical reaction of corrosion of the encapsulated sensitive chemical compound (active and intelligent additive) in contact with a reactive chemical compound. As a result of the corrosion there are released electrons and/or photons to the surface of the active and intelligent additive. When the active and intelligent additive is dispersed in a polymeric medium, these electrons released in the corrosion reaction will freely migrate to the polymer surface, providing both antimicrobial characteristics and analyte-identifying characteristics.

Thus, when the additive according to the present invention is dispersed/incorporated in a polymeric matrix, the polymer may be used, among other applications, for the manufacture of packages that are both active (antimicrobial action) and intelligent (identification and communication of the presence of analytes by way of color change and/or quantification of the electrons having been generated and/or quantification of the protons having been generated). There may be viewed below a scheme of this corrosion reaction and the products that are generated thereby:

$$A+B \rightarrow C+e^-+h\upsilon$$

Wherein:
A=Active and intelligent additive (comprising a sensitive chemical compound+capsule);
B=Reactive chemical compound;
C=Active and intelligent additive that does or does not change color;
$e^-$=Electrons released in the reaction;
$h\upsilon$=Photons released in the reaction.

SUMMARY OF THE INVENTION

The present invention relates to active and intelligent additives, formed by a sensitive compound encapsulated in an inorganic matrix with hybrid characteristics, that are thermally and mechanically stable and are capable of releasing electrons and/or photons in the presence of chemical compounds.

For a better understanding of the invention, in the present specification the following terms and/or expressions should be understood as described below herein:

Corrosion: a chemical reaction whereby are released electrons and/or photons that become available for migration;

Sensitive chemical compound: any compound capable of releasing electrons and/or photons in the presence of a reactive chemical compound, the said sensitive chemical compound being preferably selected from among copper (I), sulfur, ascorbic acid and citric acid;

Reactive chemical compound: any compound present in the medium that activates the sensitive compound, wherein the said reactive chemical compound is preferably selected from among amino compounds, amide compounds, water, oxygen reducing agents, and/or vapors thereof;

Hybrid capsule: a capsule formed by titanium or silicon alkoxides obtained by means of a sol-gel reaction;

Sol-gel reaction: a hydrolytic reaction via basic or acidic catalysis or a non-hydrolytic reaction catalyzed by a Lewis acid ($FeCl_3$, $AlCl_3$, etc.);

Hydrolytic reaction: a reaction employing titanium or silicon alkoxides, water, an acid or a base, conducted at controlled temperature, time and stirring rates;

Non-hydrolytic reaction: a reaction employing titanium or silicon alkoxides, silicon tetrachloride ($SiCl_4$), Lewis acid, conducted at controlled temperature, time and stirring rates;

Hybrid: a compound having both polar and non-polar characteristics (organic-inorganic), since the alkoxide used for encapsulation has a polar inorganic end (silicon or titanium) that interacts with the sensitive compound, and a non-polar organic chain that interacts with the matrix (polymer);

Mechanical stability: A characteristic of the active and intelligent additive that protects the sensitive chemical compound from the polymer processing conditions (shearing forces produced by the processing machinery);

Thermal stability: A characteristic of the active and intelligent additive that protects the sensitive chemical compound against degradation or decomposition arising from the high temperature at processing conditions.

Thus, the active and intelligent additives according to the present invention comprise, particularly, a sensitive compound contained within a hybrid capsule, wherein the capsule, in addition to providing mechanical and thermal stability to the sensitive compound, allows the transfer of the generated electrons and/or photons to the surface, and also improves the compatibility with the non-polar polymers, preferably polyolefinic polymers, more preferably polyethylenes and polypropylenes.

The silicon alkoxides used in the present invention are preferably the tetraethyl orthosilicate, ethyl triethoxysilane, methyl triethoxysilane, phenyl triethoxysilane, methyl trimethoxysilane, n-octyl ethoxysilane, n-butyl ethoxysilane and vinyl trimethoxysilane. The titanium alkoxides used in the present invention are preferably tetraethoxy titanium, ethyltriethoxy titanium, methyltriethoxy titanium, phenyltriethoxy titanium, n-octylethoxy titanium, n-butylethoxy titanium.

The hybridism is warranted according to the type and number of substitutions in the structure of the alkoxide used. It is important to point out that the alkoxides used are substituted with alkyl groups. The alkyl groups are accountable for a better compatibility of the additive with the polymeric matrix and in aiding to carry and expel the electrons to the surface of the matrix, preferably when comprising groups having at least one double bond in their structure.

The sensitive compounds set forth in Table 1 constitute preferred examples of compounds that may be used in the preparation of the active and intelligent additive according to the present invention. The sensitive compounds release a certain amount of electrons according to the characteristic reaction for each compound.

Such active and intelligent additive, when used as an antimicrobial agent, has the advantage, in comparison with other additives already commercially known as antimicrobial agents (silver salts, Triclosan, etc.), of not requiring direct contact of the additive with the microorganisms, since the antimicrobial effect is provided by the electrons that were released to the surface of the article, and the interaction of the electrons with the outer membrane of the microorganism or fungus (peptidoglycan, n-acetyl glucosamide, n-acetyl muranic acid) causes the rupture of the membrane and the subsequent death of the microorganism or fungus. In addition, the intelligent additive according to the present invention is not toxic, and it is possible to use the same in foodstuffs packages, and allows the active and/or intelligent film to be directly manufactured without requiring extra

TABLE 1

Characteristics of the sensitive compounds used in the preparation of the additive.

| Sensitive Compounds | Chemical Structure | Number of Electrons Released | Decomposition Temperature of the Sensitive Compound (° C.) | Decomposition Temperature of the Additive (encapsulated sensitive compound) (° C.) |
|---|---|---|---|---|
| Copper (I) Salts | $Cu^+$ | 1 | >700 | >700 |
| Sulfur Salts | $S_8$ | 6 | 100 | 246 |
| Ascorbic Acid | (structure) | 2 | 190 | 241 |
| Citric Acid | (structure) | 1 | 175 | 230 |

The polymeric matrix according to the present invention is preferably comprised of non-polar polymers, preferably polyolefinic polymers, more preferably polyethylenes and polypropylenes, since the active and intelligent additive according to the present invention evidences compatibility with the polyolefin matrix due to its hybrid functionality. The hybrid matrix further presents the advantage of withstanding the extrusion conditions (200° C.) required for the preparation of the mixture.

The release of electrons and/or photons from the intelligent additive when dispersed in the polymeric matrix occurs when the polymer is in the presence of compounds of the amino, amide, or oxygen-reducing types or vapors thereof, as well as in the presence of any substance that might generate volatile or non-volatile oxygen-reducing compounds. Those substances, on interacting with the additive, cause the latter to release electrons and/or photons into the medium (polymer). Preferably when the medium is a polyolefin matrix, due to the difference in polarity (charge) between the electron and the polyolefin, the free electrons will tend to preferably migrate to the surface of the article.

The identification of the analyte is achieved by means of the color change caused by the release of electrons, as will be better explained in the examples below herein. Furthermore, the free electrons may additionally modify the electrical conductivity or resistance of the materials.

steps to such end. Furthermore, the present invention also relates to the products obtained from the incorporation of active and intelligent additives to polymeric matrices, that is, special polymeric compositions, as well as the respective articles, which exhibit specific properties for different applications.

Particular articles contemplated by the materials of the present invention include articles that can act as antimicrobial articles and/or as colorimetric indicators (e.g., parts or protective films for these parts: handrails, door knobs, toys, garden furniture, remote control, children's lunchbox, plastic containers, sanitary seats, zip locks, water boxes, sanitation for animals, medical devices/packaging, agroindustry (silo bags), smart windows, food packaging, packaging for healthcare, domestic utilities, safety masks, ammonia leakage indicators, corrosion detection devices, sanitation for cats (e.g., for indication of urea/sand change).

EXAMPLES

Figure 1:
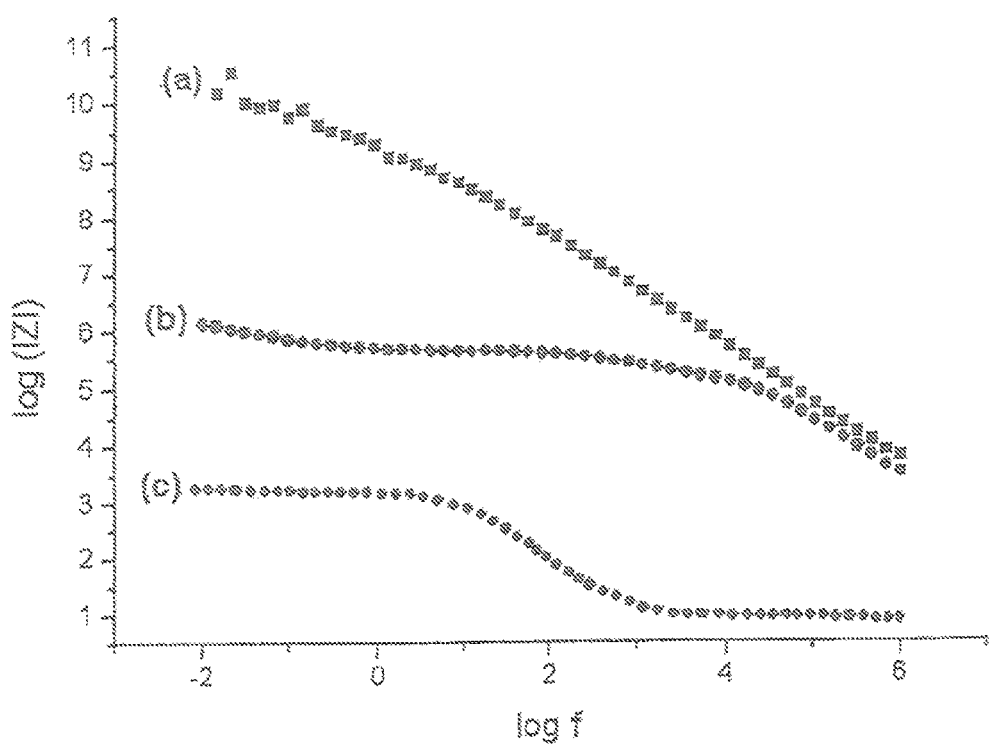
FIG. 1 is a Bode Graph obtained by EIS [Electrochemical Impedance Spectroscopy], commonly used to analyze the changes in electrical resistance of materials, wherein the electrochemical impedance module is compared against the sine wave frequency, and shows the change of electrical resistance of the polymeric film comprising the active and intelligent additive after exposure to the ammonia vapors.

The examples described herein relate to preferred embodiments of the present invention, and are thereby provided for purposes that are merely illustrative rather than limitative, so they should not be construed to constitute restrictions or to limit the scope of the present invention, whereby the latter should be interpreted in accordance with the scope of the claims attached herein.

The examples to follow are related to the obtainment of the active and intelligent additives, the activity thereof in identifying some analytes and the incorporation of such additives into polymer matrices.

Obtainment of the Active and Intelligent Additive

In general, in a preferred embodiment of the present invention, the active and intelligent additives are obtained by way of the following steps:

a) Preparation of a solution of the sensitive compound by dissolving a certain amount of this compound in a certain amount of solvent that constitutes the reaction medium itself. The amount of the sensitive compound vary from 0.005 grams to 1,000 grams dissolved within the range of from 1.0 mL to 100 L, at ambient temperature, whereby are obtained wide ranges of concentration.

b) Addition of the compounds obtained from the sol-gel reaction to item (a). Initially the pH value is conditioned by means of the addition of an acid or a base, as known in the art. Upon establishing the desired pH value, there are added the determined titanium or silicon alkoxides to generate the encapsulation of the electron-releasing compound (sensitive compound). The encapsulation by means of the addition of titanium or silicon alkoxides occurs by means of the control of the type of alkoxides, pH, temperature, time and the alkoxides/water ratio. With the determination of these variables there is controlled the relative percentage of organic and inorganic groups, that is, the degree of hybridism thereof.

c) Drying the suspension having been generated (if the active and intelligent additive was added in the form of powder).

The active and intelligent additive prepared in steps a, b and c, when dispersed in polymeric matrices, will evidence the releasing of electrons and/or photons upon interacting with amino, amide or oxygen reducing substances, either or not in the form of vapor. In addition it evidences a good dispersion ability and good compatibility as provided by the hybrid characteristic of the additive and by its thermal and mechanical stability.

The active and intelligent additive according to the present invention may be used as an antimicrobial agent, an indicator of the presence of an analyte, an indicator of communication (may be detected with the presence of a chip or another common electronic means), a generator of energy, an electrical conductor or electrical resistance reducer of a specific material, or for any other application that might require the presence of free electrons.

1—Preparation of the Active and Intelligent Additive in the Form of Powder and Provision of Evidence of the Release of Electrons and of Color Change The active and intelligent additive was obtained in accordance with the following methodology: 1.0 g of the sensitive compound (copper I chloride) was dispersed in a mixture of 5 mL of deionized $H_2O$ and 0.1 mL of concentrated HCl. Thereupon there were added thereto 4 mL of TEOS (tetraethyl orthosilicate) and 6 mL of OTMSi (octyl trimethoxysilane), or MTMSi (Methyl trimethoxysilane), or VTMSi (vinyl trimethoxysilane). The organosilanes reacted for 1 hour at ambient temperature and being subjected to mechanical stirring. Upon that time having elapsed, the solid product was ground until the particle size thereof reached the micron range and was washed with water until the washing residue became colorless, and was subsequently dried in an oven at 80° C. There was finally obtained an active and intelligent additive in the form of powder and having a greenish hue ($Cu^+$).

For purposes of evidencing the active and intelligent action thereof, the additive obtained in Example 1 above was subjected to a basic gas ($NH_3$) at ambient temperature. The solid obtained thereby acquired a bluish color ($Cu^{2+}$) on reacting with ammonia, thereby evidencing the release of electrons by the copper oxidation reaction and the identification of amino compounds by the change in color, at ambient temperature.

The release of electrons took place by way of the following reaction:

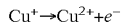

$$Cu^+ \rightarrow Cu^{2+} + e^-$$

As previously set forth, the electron release may be used for the function of antimicrobial agent in an active package, and the color change may be used in an intelligent package for visual detection of an analyte. For example, foodstuffs undergoing a putrefaction process usually release amino compounds such as ammonia, due to the action of bacteria and fungi that transform the amino acids into gasses, and the electrons release in this case points out the presence of the ammonia by way of the change of color of the copper and further attacks the bacteria present therein, as previously explained, evidencing thereby an intelligent action (identification of the analyte by color change) and an active (antimicrobial) action.

2—Incorporation of the Active and Intelligent Additive into the Polymeric Matrix and Evidencing the Release of Electrons and the Change in Color The incorporation of the active and intelligent additive into the polymeric matrix was performed using standard extrusion procedures for polymer processing, such as temperature profile, type of thread and type of extruder normally used in an additivation process. Upon the incorporation of the active and intelligent additive into the polymer, there were fabricated films using a balloon-type film extruder, where the thickness of the films was between 10 and 100 μm.

The evidence of release of the electrons by the active and intelligent additive after incorporation of the same into the polymeric matrix was provided by the change in Electric (Ohmic) Resistance of the films. The electrical resistance property is characteristic for each type of material, as are the fusion heat, the density, etc. To such end, the films were exposed to ammonia vapors and were compared with the films that were not subjected to exposure to the ammonia vapors. The measurements of electrical resistance were made using the Electrochemical Impedance Spectroscopy (EIS) technique, which consists in the excitation of an electrochemical cell by a sine wave signal and the respective analysis of the current produced thereby. By means of the due mathematical treatment of that response, one is able to obtain the Impedance and the Ohmic Resistance of the material that is being subjected to measurements.

The graph of FIG. 1 represents the module of electrochemical impedance as a function of the frequency of the sine wave, wherein there may be observed the curve (a) which represents the impedance of the film with the additive incorporated therein, the curve (b) which represents the impedance of that same film, however in contact with $NH_3$ gas, and the curve (c) which corresponds to the metallic copper (for purposes of comparison with conductive metals). There may be also noted an ample decrease of impedance of the film having the active and intelligent additive incorporated therein, in the presence of vapors of ammonia ($NH_3$), when compared with the film with no presence of $NH_3$. The polymeric film without the addition of the active and intelligent additive does not evidence any kind of change, since this is a property of the material and it is not affected by an external chemical action.

If compared with the curve (c) of the metal, we may note that, relatively to the presence of ammonia, the behavior of the film including the additive approximates the behavior of a metal, in what concerns the presence of electrons on the surface.

In Table 2 one may observe the decrease in electrical resistance of the described materials, once again confirming the release of electrons when in contact with the vapors of an analyte (ammonia). The former evidences the functioning of the active and intelligent additive when dispersed in a polymeric matrix, functioning as a releaser of electrons, which provides thereto suitability for all the applications that have been previously described herein. It may be noted that for the described films, the electrical resistance decreases in the order of $10^3$ to $10^4$ Ohms when in the presence of $NH_3$ gas. This is caused by the release of electrons from each of the different films having been fabricated.

When compared with the pure film devoid of additive, one may observe that the decrease of electrical resistance of the film with the active and intelligent additive incorporated therein, in the presence of ammonia, is about 100 to 1000 times. The former shows that the active and intelligent additive has the ability to change the electrical resistance characteristics of the materials, providing a wide range of new applications. The former could present distinct applications such as a switch, which in the presence of a certain analyte allows the communication of specific environment conditions, either by way of the release of electrons or by changing color.

TABLE 2

Decrease of the electrical resistance of the films by the release of electrons.

| Film | Electrical resistance | Electrical resistance in the presence of $NH_3$ vapor |
|---|---|---|
| Pure film without additive | $6.7 \times 10^{10}$ Ω | $1.5 \times 10^9$ Ω |
| Film with additive based on citric acid | $7.0 \times 10^9$ Ω | $1.1 \times 10^5$ Ω |
| Film with additive based on sulfur | $1.6 \times 10^9$ Ω | $3.0 \times 10^5$ Ω |
| Film with additive based on copper (I) | $6.2 \times 10^9$ Ω | $2.2 \times 10^6$ Ω |

This demonstrates the presence of free electrons in the polymeric film when arising from the contact of the active and intelligent additive with an analyte (ammonia vapor).

3—Evidence of the Antimicrobial Action of the Films Whereto was Added the Active and Intelligent Additive.

The methodology used to determine the antimicrobial effect was practiced by means of the total bacteriological count of microorganisms, specifically *Pseudomonas*, varying the shelf storage time of the foodstuff.

Method: Pieces of chicken breast of approximately 50 grams each were packaged with the films provided with the active and intelligent additive. These films, containing the chicken breasts, were sealed in the form of bags, thereby simulating the shelf storage conditions of the packaged foodstuff. Subsequently the said bags containing the chicken breasts were packaged in a secondary bag of polyolefin film (without the incorporation of the active and intelligent additives) using vacuum (the same test may be conducted using a film co-extruded with an additive-bearing layer and a layer with no additive). The innermost layer, which contains the additive, is intended for the purpose of perceiving the electrons released by the volatile compounds produced by the degradation of the foodstuff and to promote the migration thereof to the surface of the film which is in direct contact with the foodstuff (innermost surface) rather than to the outer part, in which, in this specific case, it would not evidence any advantage, being devoid of antimicrobial efficiency (which would occur by means of the loss of the electrons to the external surface). Subsequently to the packaging, there were conducted the analyses of counting of *Pseudomonas* once every three days to determine the microbiological growth as a function of time and to observe the antimicrobial action of the polymeric films additivated with the active and intelligent additives.

Figure 2:
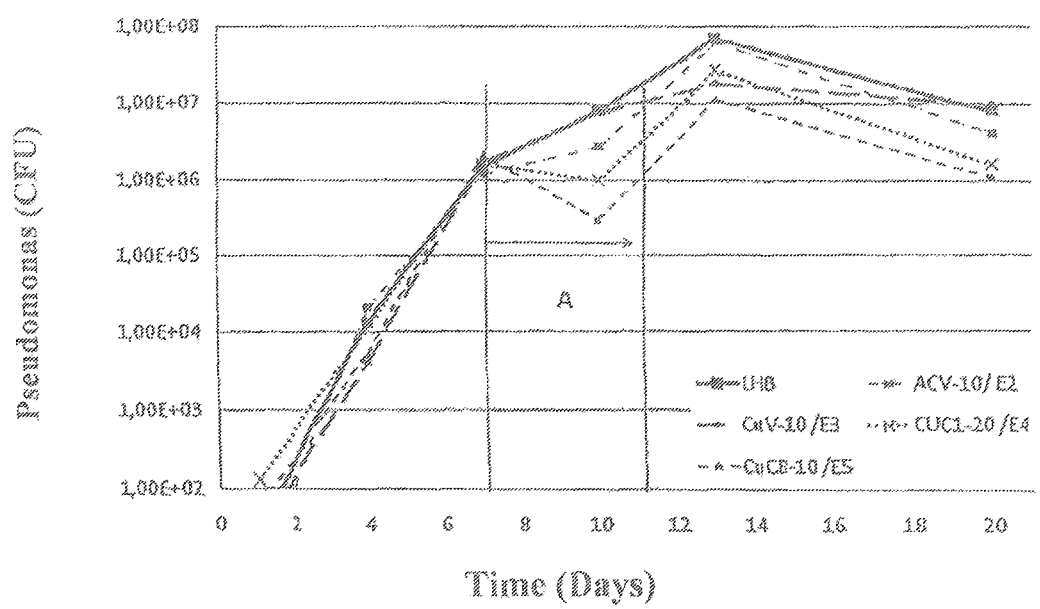
FIG. 2 illustrates a graph that reflects the microbiological growth of *Pseudomonas* against shelf storage time in samples of chicken packaged with additive films using the active and intelligent additive.

In the graph of FIG. 2, the samples used for the study were the following:

LHB: Polyolefin film (without incorporating the active and intelligent additive).

CuV-10/E3: LHB with the incorporation of the Copper-based active and intelligent additive and a hybrid ratio TEOS/VTMSi (vinylic)

CuC8-10/E5: LHB with the incorporation of the Copper-based active and intelligent additive and a hybrid ratio TEOS/OTMSi (octyl)

CuC1-20/E4: LHB with the incorporation of the Copper-based active and intelligent additive and a hybrid ratio TEOS/MTMSi (methyl)

ACV-10/E2: LHB with the incorporation of the Citric Acid-based active and intelligent additive and a hybrid ratio TEOS/VTMSi (vinylic)

There may be noted an exponential growth of the *Pseudomonas* that was equal for all samples up until the seventh day, when there was reached a concentration of $1 \times 10^6$ UFC. After 7 days, the samples of CuC8-10/E5, CuC1-20/E4 and ACV-10/E2 evidenced a reduction in the growth of the *Pseudomonas*. The sample CuC8-10/E5 evidenced the best behavior in reducing the growth of *Pseudomonas*, and specifically with this sample there was once again achieved the value of $1 \times 10^6$ UFC on the $11^{th}$ day. These results clearly show the microbiological growth inhibiting effect in the samples of film comprising the active and intelligent additives. Specifically, the sample that evidenced a greater level of efficiency in reducing the microbiological growth was the sample identified as CuC8-10/E5. This constitutes extremely strong proof of the effect as inhibitor of microbiological growth of *Pseudomonas* in samples of chicken breast, when the latter were packaged using the films that were additivated using the active and intelligent additives according to the present invention. Thus, there may be established an increase of 4 days in the useful time of the said foodstuff and there has been demonstrated the use of the packages made with these films provided with the additives according to the present invention as constituting active and intelligent packages.

The reduction of growth of *Pseudomonas* was due to the release of the electrons contained in the active and intelligent additives, which when placed in contact with the gasses produced by the decomposition of the chicken, evidence the release of electrons, whereby the cited electrons interact with the *Pseudomonas*, inhibiting the growth of the latter.

All documents cited in the present document are incorporated hereto for purposes of reference, as regards the relevant part thereof. The citation of any document should not be construed as an admission of the fact that the same might represent prior art with relation to the present invention. Although there were illustrated in the examples and drawings attached hereto, and described in the instant specification, some preferred embodiments of the invention, it should be obvious to a technician skilled in the art that the invention is in no way limited to the realizations thereof as described herein, and there should be rather construed that other alterations, modifications and substitutions may be made without deviating from the characteristic nature and scope of the invention, which is defined in the claims attached hereto.

The invention claimed is:

1. A polyolefin material comprising an active and intelligent additive incorporated within the polyolefin material, wherein said active and intelligent additive is formed of a sensitive compound encapsulated in an inorganic matrix with hybrid characteristics, said inorganic matrix with hybrid characteristics formed by a silicon alkoxide or a titanium alkoxide, wherein said sensitive compound releases electrons and/or photons as an antimicrobial agent in the presence of a reactive chemical compound by means of a reaction of corrosion of the encapsulated sensitive compound, said reactive chemical compound comprising any compound present in a medium that activates said sensitive compound, wherein said sensitive compound is selected from the group consisting of copper (I), sulfur, ascorbic acid and citric acid, and wherein said silicon alkoxide is selected from the group consisting of tetraethyl orthosilicate, ethyl triethoxysilane, methyl triethoxysilane, phenyl triethoxysilane, methyl trimethoxysilane, n-octyl ethoxysilane, n-butyl ethoxysilane and vinyl trimethoxysilane, and said titanium alkoxide is selected from the group consisting of tetraethoxy titanium, ethyltriethoxy titanium, methyltriethoxy titanium, phenyltriethoxy titanium, n-octylethoxy titanium and n-butylethoxy titanium, and wherein the material with the additive has antimicrobial activity.

2. The polyolefin material as recited in claim 1, wherein said reactive chemical compound is selected from the group consisting of amino compounds, amide compounds, oxygen-reducing compounds and/or vapors thereof.

3. The polyolefin material as recited in claim 1, wherein said polyolefin is a polyethylene.

4. The polyolefin material as recited in claim 1, wherein said polyolefin is a polypropylene.

5. The polyolefin material as recited in claim 1, wherein said additive acts as an indicator of gas presence.

6. The polyolefin material as recited in claim 1, wherein said additive acts as a colorimetric indicator.

7. An active and intelligent article, comprising the polyolefin material as recited in claim 1.

* * * * *